(12) United States Patent
Rotella et al.

(10) Patent No.: US 7,850,714 B2
(45) Date of Patent: Dec. 14, 2010

(54) SEGMENTED TISSUE-TO-TISSUE ANCHORING DEVICE AND METHOD OF USING THE SAME

(75) Inventors: John A. Rotella, Alpharetta, GA (US); Donald J. McMichael, Roswell, GA (US); Luis A. Davila, Alpharetta, GA (US); Alphonse DeMarco, Tucson, AZ (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 802 days.

(21) Appl. No.: 11/640,449

(22) Filed: Dec. 15, 2006

(65) Prior Publication Data

US 2008/0147102 A1  Jun. 19, 2008

(51) Int. Cl.
*A61B 17/04* (2006.01)
(52) U.S. Cl. .................................................. 606/232
(58) Field of Classification Search .................. 606/232
See application file for complete search history.

(56) References Cited

U.S. PATENT DOCUMENTS

| | | | |
|---|---|---|---|
| 4,449,532 A | | 5/1984 | Storz |
| 4,741,330 A | * | 5/1988 | Hayhurst .................... 606/144 |
| 4,862,891 A | | 9/1989 | Smith |
| 4,968,315 A | * | 11/1990 | Gatturna .................... 606/139 |
| 5,041,129 A | * | 8/1991 | Hayhurst et al. ............ 606/232 |
| 5,139,486 A | | 8/1992 | Moss |
| 5,158,543 A | | 10/1992 | Lazarus |
| 5,176,682 A | * | 1/1993 | Chow ......................... 606/232 |
| 5,203,787 A | * | 4/1993 | Noblitt et al. ............... 606/232 |
| 5,292,311 A | | 3/1994 | Cope |
| 5,324,308 A | * | 6/1994 | Pierce ........................ 606/232 |
| 5,389,090 A | | 2/1995 | Fischell et al. |
| 5,403,348 A | * | 4/1995 | Bonutti ....................... 606/232 |
| 5,405,359 A | * | 4/1995 | Pierce ........................ 606/232 |
| 5,464,426 A | * | 11/1995 | Bonutti ....................... 606/232 |
| 5,464,427 A | * | 11/1995 | Curtis et al. ................ 606/232 |
| 5,486,197 A | * | 1/1996 | Le et al. ..................... 606/232 |
| 5,499,975 A | | 3/1996 | Cope et al. |
| 5,522,846 A | * | 6/1996 | Bonutti ....................... 606/232 |
| 5,536,255 A | | 7/1996 | Moss |

(Continued)

FOREIGN PATENT DOCUMENTS

EP  0 383 426 A1  8/1990

(Continued)

OTHER PUBLICATIONS

International Search Report and Written Opinon, Apr. 11, 2008.

*Primary Examiner*—(Jackie) Tan-Uyen T Ho
*Assistant Examiner*—Son Dang
(74) *Attorney, Agent, or Firm*—Dority & Manning, P.A.

(57) ABSTRACT

The invention describes an apparatus and method of use for anchoring two or more body tissue layers to one another. The apparatus includes a plurality of individual anchor segments that are placeable within a body cavity. The segments may assume a first relaxed state wherein the segments are movable relative to each other and alignable along an initial longitudinal axis for initial placement of the apparatus through the body tissue layers. Once placed within the body cavity, the anchor segments are manipulated into a second rigid state with an actuator wherein the segments assume a rigid configuration at a transverse angle relative to the initial longitudinal axis.

17 Claims, 5 Drawing Sheets

U.S. PATENT DOCUMENTS

| | | | |
|---|---|---|---|
| 5,584,862 A * | 12/1996 | Bonutti | 606/232 |
| 5,733,306 A * | 3/1998 | Bonutti | 606/232 |
| 5,941,900 A * | 8/1999 | Bonutti | 606/232 |
| 6,056,773 A * | 5/2000 | Bonutti | 606/232 |
| 6,077,292 A * | 6/2000 | Bonutti | 606/232 |
| 6,149,669 A * | 11/2000 | Li | 606/232 |
| 6,152,949 A * | 11/2000 | Bonutti | 606/232 |
| 6,206,886 B1 * | 3/2001 | Bennett | 606/104 |
| 6,287,325 B1 * | 9/2001 | Bonutti | 606/232 |
| 6,309,405 B1 * | 10/2001 | Bonutti | 606/232 |
| 6,312,448 B1 * | 11/2001 | Bonutti | 606/232 |
| 6,364,897 B1 * | 4/2002 | Bonutti | 606/232 |
| 6,428,562 B2 * | 8/2002 | Bonutti | 606/232 |
| 6,656,183 B2 * | 12/2003 | Colleran et al. | 606/232 |
| 2004/0059339 A1 | 3/2004 | Roehm, III et al. | |
| 2006/0004398 A1 | 1/2006 | Binder, Jr. et al. | |

FOREIGN PATENT DOCUMENTS

| | | |
|---|---|---|
| EP | 0 522 735 A1 | 1/1993 |
| EP | 0 556 618 A1 | 8/1993 |
| EP | 0 699 416 | 3/1996 |
| WO | WO 03/061751 A1 | 1/2003 |
| WO | WO 03/096910 | 11/2003 |
| WO | WO 2005/089658 | 9/2005 |
| WO | WO 2006/111394 A2 | 10/2006 |

* cited by examiner

SEGMENTED TISSUE-TO-TISSUE ANCHORING DEVICE AND METHOD OF USING THE SAME

FIELD OF THE INVENTION

The present invention relates to a device for anchoring a first body tissue to one or more additional body tissue layers. Such a device may be used, for example, to anchor a patient's stomach wall to the abdominal wall prior to use of a gastronomy feeding tube used in the direct feeding of a patient's stomach. More particularly, the present invention may be used in procedures related to percutaneously placing various gastric catheters, forming artificial stomas capable of accessing the gastrointestinal tract, and otherwise securing two or more tissue layers to one another until such time as the tissue layers fuse to one another.

BACKGROUND OF THE INVENTION

It is recognized that numerous medical conditions exist in which it becomes necessary to gain percutaneous access to viscera such as the stomach or small intestines. Situations where a patient has lost the ability to swallow and will require long term nutritional support may dictate feeding directly into the stomach or jejunum. Feeding in this manner may be accomplished by inserting a feeding tube into the patient's stomach such that one end remains anchored in the stomach, while the other end remains external to the patient's body for connection to a nutrient source. Such feeding tubes may be inserted into a patient's stomach in a number of ways. For example, the feeding tubes may be endoscopically placed, surgically placed through an open incision, laparoscopically placed, or percutaneously placed under endoscopic, fluoroscopic or ultrasonic guidance. ifferent types of feeding tubes may be placed using these procedures, including gastrostomy, jejunostomy or gastro-jejunostomy tubes. These tubes may be retained in the lumen (stomach or intestine) with a variety of retention anchors. These anchoring mechanisms include: inflatable balloons, obturatable domes, fixed dome-type bumpers, or suture wings.

Prior to placing the actual enteral feeding device, it is generally necessary to perform a gastropexy procedure wherein the stomach wall is drawn against the abdominal wall at a location where the stoma tract will be eventually defined. This attachment is critical to prevent inadvertent separation and exposure of the peritoneal cavity to contamination and possible peritonitis.

Initial placement devices are often not readily removable without additional invasive procedures. That is, many initially placed anchoring devices contain rigid retention members that are not readily removable without additional procedures. These retention members are typically rigid T-shaped or H-shaped metal fasteners (collectively referred to as a "T-bar") and are not removable, but are allowed to pass naturally in the patient's stool. In many cases, however, the T-bar is not passed and remains within the body cavity. Moreover, during the six to eight weeks it takes for the fistula's stoma tract to be established, the T-bar of the prior art gastropexy device may embed itself into the gastric or intestinal wall and ultimately lead to infection. Furthermore, the T-bar itself may have sharp edges which can be uncomfortable for the patient.

In many of these procedures, in order to achieve the desired seal between the stomach and the abdominal wall, a traction force must be applied to the anchoring mechanism. The force is applied in such a way as to pull the stomach cavity to the abdominal wall so that the penetration through both may heal together, resulting in the tissue layers essentially adhering to each other. It is necessary to apply this traction force for a period of a couple of days through a couple of weeks until the attachment forms and stoma site adequately heals. During this period the patient has reduced mobility which may lead to additional post-operative complications.

There is thus a need and desire for an improved tissue anchoring device that may be used during initial placement or creation of a stoma site. Such a device would foster the permanent fusion of the stomach wall to the abdomen. This would serve to reduce the invasiveness of the procedure, greatly enhance wound healing, and enable immediate, post-placement gastric access for feeding and drainage, and ultimately allow a traumatic exchange of the low profile device. What is needed is a fixation device that is easy to place within an internal body cavity, allows for the formation of a stoma between the internal body cavity and the external environment, and enables the user to easily remove the fixation device when it is no longer necessary.

SUMMARY OF THE INVENTION

Objects and advantages of the invention will be set forth in part in the following description, or may be obvious from the description, or may be learned through practice of the invention.

The present invention is directed toward an apparatus for insertion into a body orifice for anchoring a first body tissue layer to a second body tissue layer. In a particular embodiment, the apparatus includes a plurality of individual substantially rigid anchor segments that are designed for insertion through at least two body tissue layers and into a body orifice from a point exterior to the body orifice. The anchor segments may be introduced through the tissue layers and into the body cavity through a hollow needle or trocar-type introducer wherein the anchor segments are longitudinally aligned in a first relaxed state and are movable relative to each other. The anchor segments can be manipulated into a second rigid state within the body cavity wherein the segments assume a rigid configuration relative to each other and extend at a transverse angle relative to their initial aligned longitudinal axis. For example, at least two transverse branches of anchor segments may extend perpendicular from the initial longitudinal axis, with at least one anchor segment in each branch. The branches may extend from a central anchor segment, with one or more segments in each branch.

The anchor segments may take on any suitable shape and configuration, and are desirably void of sharp angles or corners to minimize any discomfort to the patient. In a particular embodiment, the anchor segments are substantially cylindrical elements with a passage therethrough.

An actuator is connected to the anchor segments and extends through central anchor segment to the distal end of the last anchor segment in each branch. The actuator provides a means for a clinician to externally manipulate the anchor segments from their first relaxed state to the second rigid state. In a particular embodiment, the actuator includes a respective filament that extends through the central anchor segment shaft to each branch of anchor segments, and is fixed to an end of the last anchor segment in each transverse branch. The filaments extend through the tissue layers, with the opposite ends of the filaments extend externally from the body. These ends are pulled or otherwise tensioned by the clinician to draw the anchor segments against into the second rigid state. It should be appreciated that "filament" is used herein to refer to any flexible elongated member that is connected to the anchor segments and extends through the tissue layers to actuate the apparatus.

In a particular embodiment, the apparatus may include two transverse anchor segments and a central anchor segment, with each transverse anchor segment extending in a transverse direction relative to central anchor segment. The transverse anchor segments may extend in opposite directions (i.e., 180 degrees apart) or in less than opposite directions (i.e., an angle less than 180 degrees).

In an alternate embodiment, a plurality of anchor segments are included within each transversely extending branch. For example, the apparatus may include at least two anchor segments extending in each transverse direction from a central anchor segment. In this embodiment, the individual anchor segments are disconnected and movable relative to each other in the first relaxed state of the apparatus. The actuator runs through all of the anchor segments within an individual branch and draws the segments together into a rigid configuration upon being tensioned in the second rigid state.

The anchor segments may have relatively flat adjacent faces that are brought into abutting axial alignment upon a sufficient tension being applied to the actuator. In an alternative embodiment, the end faces of the anchor segments may contain inter-engaging structure, such as any male/female engagement, that aids in aligning and maintaining the anchor members in the second rigid state. This structure may include, for example, a tapered protrusion defined on an end face of one anchor segment that engages into a correspondingly shaped slot in the adjacent end face of another anchor segment.

The anchor segments may be maintained in the second rigid state by a constant external tensioning force applied to the actuator, whereupon the anchor segments assume the first relaxed state upon release of the tensioning force.

The apparatus may further include any manner of low profile external fixing member that receives and maintains the actuator filaments in their tensioned or drawn state. This device may be a simple plate-like member with a slot or hole through which the filaments are threaded and tied off.

It may be desirable that at least one of the components of the apparatus is made from a resorbable material that breaks down over time in the patient. For example, any combination of the actuator and anchor segments may be made from such a material. The resorbable materials aid in collapsing and passing the apparatus components through the patient's digestive tract after the stoma has formed and the apparatus is no longer needed. The resorbable components break down into even smaller pieces and are readily passed through the digestive tract with less chance of becoming lodged.

The present invention also encompasses any manner of surgical method or procedure for anchoring a first body tissue layer to a second body tissue layer using aspects of the apparatus described herein. Such a method may be particularly well suited for use in performing a gastropexy procedure wherein one of the body tissue layers comprises the abdominal wall and the other layer comprises the stomach.

Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

Reference will now be made in detail to embodiments of the invention, one or more examples of which are illustrated in the drawings. Each embodiment is presented by way of explanation of aspects of the invention, and not as a limitation of the invention. For example, features illustrated or described as part of one embodiment may be used with another embodiment to yield still a further embodiment. It is intended that the invention include these and other modifications and variations as come within the scope and spirit of the invention.

The present invention is directed toward an apparatus for anchoring a first body tissue to a second body tissue and a method for using such an apparatus. Should such a device be caused to enter a body from an exterior position, traverse two or more body tissue layers, and be situated at a distal end within a suitable body cavity or orifice, the device may be used to pull the two or more tissue layers into contact thereby anchoring one to the other. The apparatus is particularly useful in a gastropexy procedure wherein the stomach wall is drawn against the abdominal wall at a location where a stoma tract will be eventually defined. This attachment is critical to prevent inadvertent separation and exposure of the peritoneal cavity to contamination and possible peritonitis.

Figure 1:
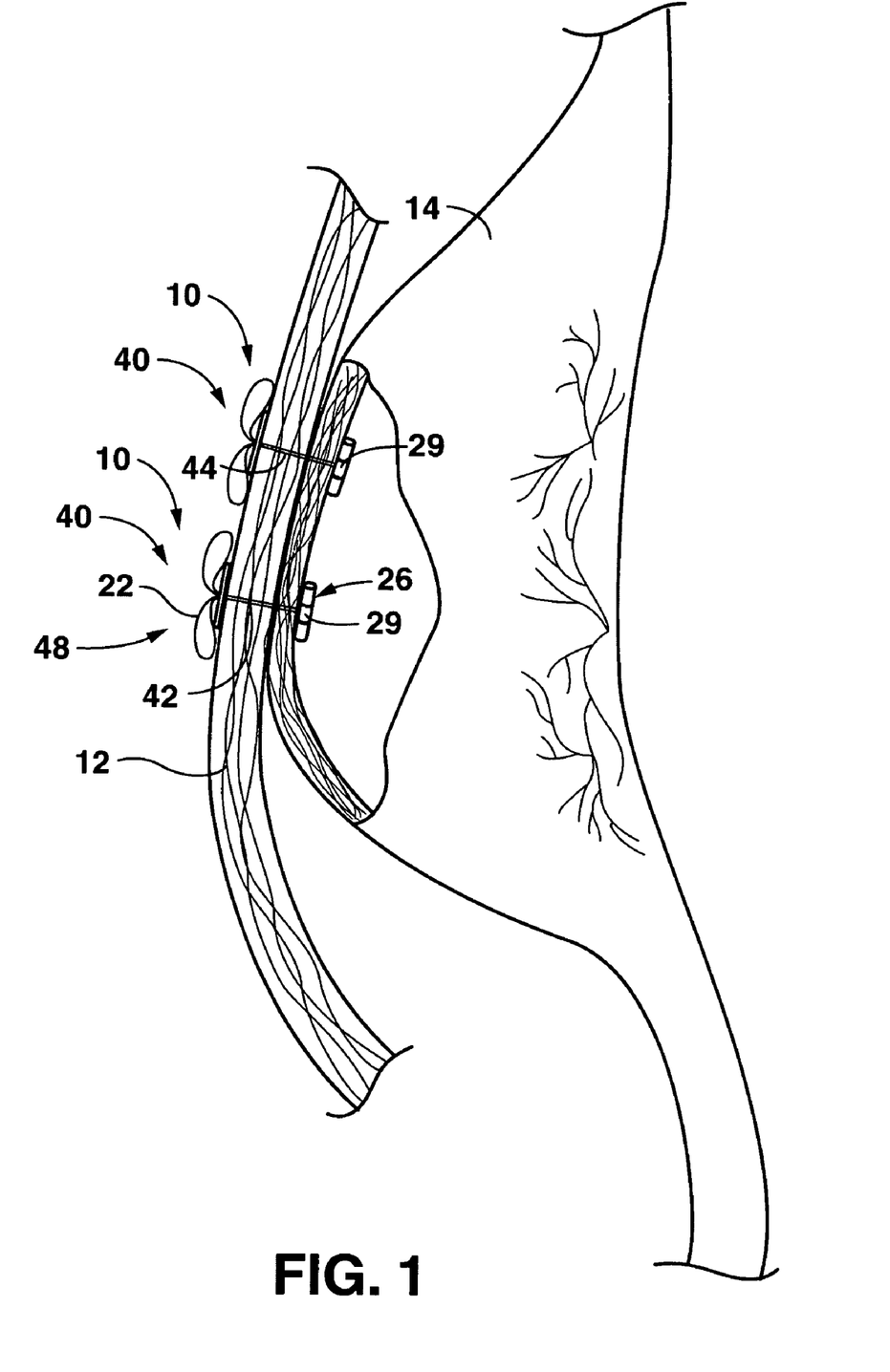
FIG. 1 depicts an illustrative view of one embodiment of the present invention inserted through a patient's abdominal wall and stomach.

FIG. 1 shows an embodiment 10 of an inventive apparatus for insertion into a body orifice or cavity for anchoring a first body tissue layer 12 to at least one other body tissue layer 14. In the illustration, the devices 10 are used to anchor abdominal wall tissue 12 to the stomach wall 14 in a gastropexy procedure for forming a feeding stoma in the patient. Each apparatus 10 includes a plurality of anchor segments 26 that have been placed into the body cavity (e.g, through the stomach wall and into the stomach). An actuator 40 is connected to the anchor segments 26 and extends through the body tissue layers 12, 14, and is used to draw the anchor segments into a rigid state wherein they extend at a transverse angle from the longitudinal axis of the actuator 40, or from opposite sides of a central anchor segment 29. The actuator 40 is secured externally to an external fixing member 48 placed against the patient, as discussed in greater detail below.

As used herein, distal refers generally to the direction of the patient, while proximal refers to the direction of the user.

The various components of the apparatus 10 may be formed from a biocompatible metal or polymeric material. Such polymeric materials may include polyurethane (PU), low-density polyethylene (LDPE), polyvinyl chloride (PVC), polyamide (PA) or polyethylene teraphthalate (PETP). Copolymer admixtures for modifying the characteristics of the material are also possible, for example a low density polyethylene and ethylene-vinylacetate copolymer (LDPE-EVA), or blends of the above mentioned materials (e.g. PU with PVC or PU with PA) would be considered suitable for such a device.

As discussed in greater detail below, any combination of the components forming the apparatus 10 may be formed partially or wholly of a resorbable material that degrades and breaks down over time. These materials are typically polymers that can be cleaved hydrolytically or by the action of enzymes, and are currently used in medical applications as sealants, sutures, staples, implants, and the like. Examples of such materials include natural or semi-synthetic polymers, including certain bone cements. The materials can be sterilized and have biocompatible (non-toxic) degradation products. A wide class of suitable resorbable materials are known to those skilled in the art. For gastropexy procedures, the resorbable materials must be able to maintain their integrity in the relatively harsh stomach environment of strong acids and enzymes for a time sufficient for the stoma to properly form, ideally about 6 weeks. Presently, it is believed that a copolymer of an aromatic polyester and a lactide; polydioxanones; or polyanhydrides may present optimal resorbable material for use in the apparatus of the present invention for gastropexy procedures.

Figures 2, 3:
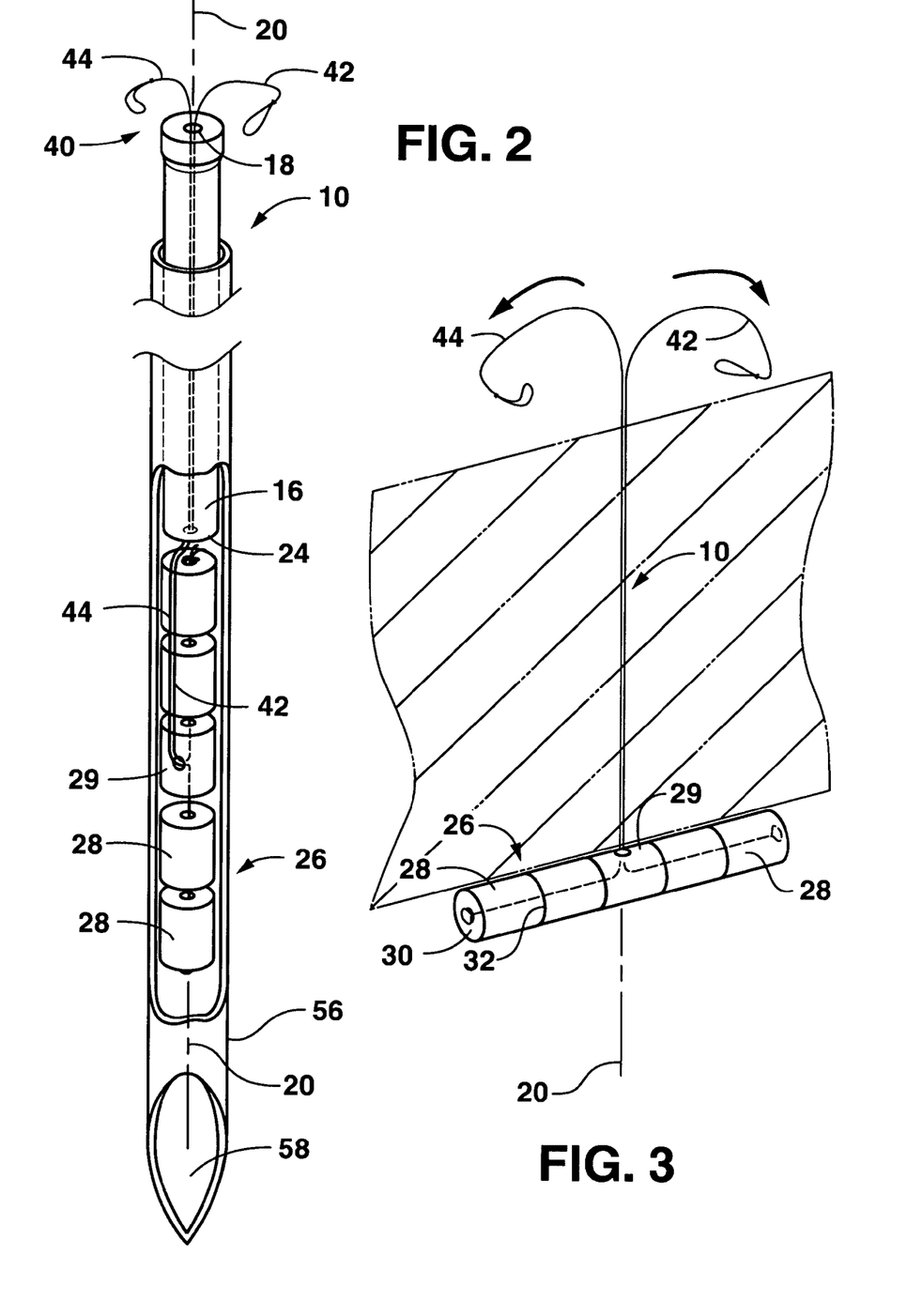
FIG. 2 is a perspective view of an embodiment of an anchoring apparatus in accordance with the invention inserted into an introducer for placement in a patient.
FIG. 3 is a perspective view of the apparatus of FIG. 2 with the anchor segments in their second rigid state.

FIG. 2 illustrates the apparatus 10 loaded into an introducer 56, which may be a trocar or needle having a bore 58 therethrough. The introducer 56 may be used to pierce the body tissue layers and for insertion of the apparatus 10 into the body cavity. Alternatively, the introducer 56 may be inserted through a previously formed puncture site.

In the particular embodiment illustrated in FIGS. 2 and 3, the anchor segments 26 include a plurality of cylindrical segments 28 having a bore therethrough. In FIG. 2, the cylindrical segments 28 are illustrated in their first relaxed state wherein the segments 28 are movable relative to each other and aligned within the introducer 56 along an initial longitudinal axis 20. In this manner, the cylindrical segments 28 are readily insertable into the introducer 56 for initial placement of the apparatus 10 through the body tissue layers.

Referring to FIG. 2, an insertion tool 16 may also be inserted into the introducer 56 to "push" the anchor segments 26 out of the introducer once the distal tip of the introducer has been inserted into the body cavity. This tool 16 may be any rigid rod-like member having a bore 18 through which the actuator 40 runs. After the anchor segments 26 have been pushed from the introducer, the introducer 56 and tool 16 may be removed while maintaining the end of the actuator 40 external to the body, as depicted in FIG. 3. The tool 16 may be removed from the introducer by simply unthreading the tool 16 from the actuator 40.

It should be appreciated that any motive force may be used to push the anchor segments 26 through the introducer 56. For example, a liquid may be injected into the introducer to force the anchor segments through and out of the introducer 56.

Once the apparatus 10 has been properly placed, the anchor segments 26 can be manipulated into a second rigid state as illustrated in FIG. 3 wherein the segments assume a rigid configuration at a transverse angle relative to the initial longitudinal axis 20. In the illustrated embodiment, at least two transverse branches of the anchor segments 26 extend at opposite perpendicular directions from the axis 20.

Figure 4:
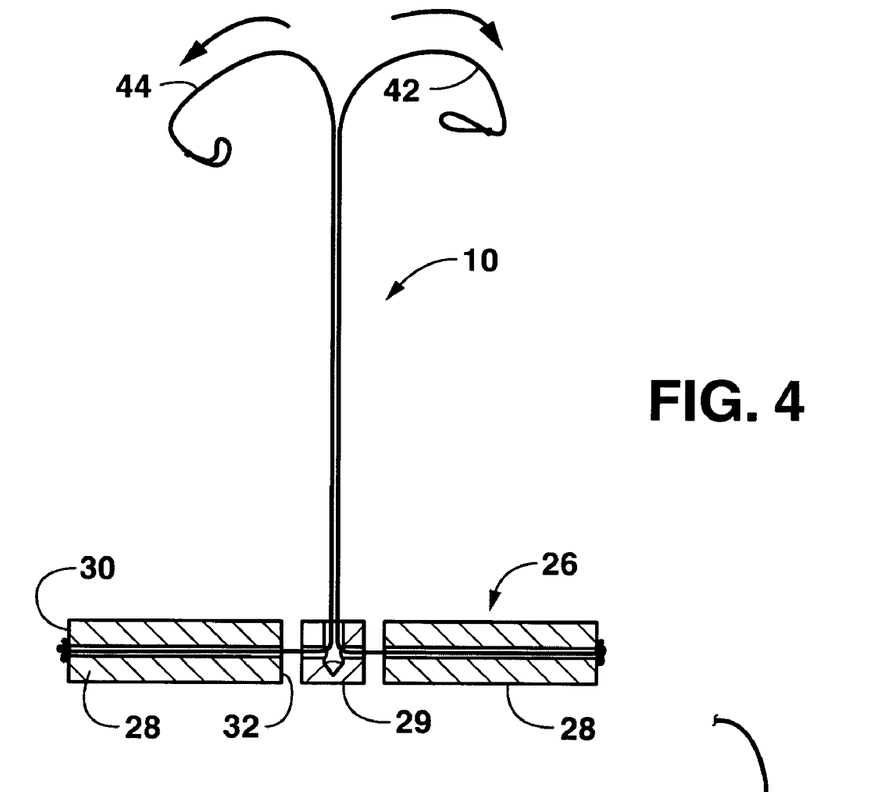
FIG. 4 is a partial cross-sectional view of an alternative embodiment of an anchoring apparatus with a single anchoring segment extending in opposite transverse directions.

Referring to FIGS. 2 and 3, a plurality of individual cylindrical segments 28 are aligned in each of the branches of anchor segments 26 on opposite sides of a central cylindrical segment 29. The actuator 40 runs through the central segment 28 to each branch of the anchor segments 26 and defines structure wherein an external vertical tensioning force applied to the actuator 40 is converted to a generally transverse force that pulls the anchor segments together towards the central segment 29. It should be appreciated that any number of the cylindrical segments 28 may be aligned within any individual branch. It should also be understood that each branch may include only a single cylindrical segment 28, as illustrated for example in FIG. 4.

The anchor segments 26 may take on any suitable shape and configuration, but are desirably void of sharp angles or corners to minimize any discomfort to the patient. The cylindrical segments 28 may be desired for this reason.

Figure 5:
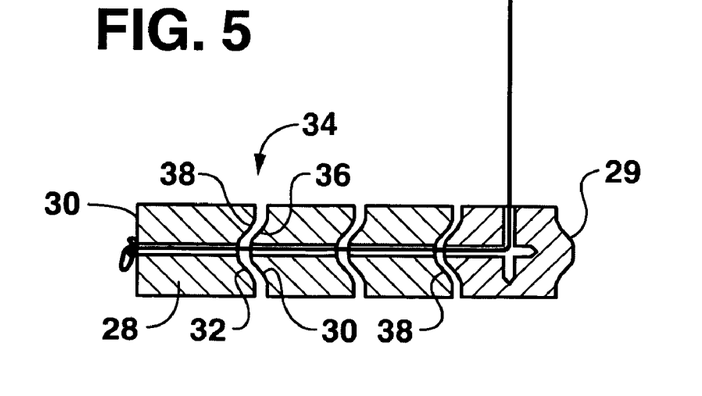
FIG. 5 is a partial cross-sectional view of an embodiment of the anchoring segments incorporating multiple anchor segments extending in opposite transverse directions with alignment structure between the individual segments.

An actuator 40 is connected to the anchor segments 26 and extends through the central segment 29 to the distal end of the anchor segments 26 in each transverse branch. The actuator 40 provides a means for the clinician to externally manipulate the anchor segments 26 from their first relaxed state illustrated in FIG. 2, to the second rigid state illustrated in FIG. 3. In a particular embodiment, the actuator 40 includes separate filaments 42, 44 that extend through the body tissue layers along the axis 20, into the central segment 29, and through the anchor segments 26 in each transverse branch. The filaments 42, 44 are fixed to the end of the last anchor segment 26 furthest from the central segment 29 in each transverse branch of anchor segments, as illustrated particularly in FIGS. 3-5. The filaments may be simply threaded through the bores in the anchor segments 26 and knotted or otherwise secured at the end face 30 of the furthest segment 26.

The opposite end of the actuator 40 extends external to the body tissue layers, as particularly illustrated in FIGS. 1 and 3. Once the anchor segments 26 have been pushed through the introducer 56 and into the body cavity, the actuator 40 (filaments 42, 44 in the illustrated embodiment) are pulled or otherwise tensioned by a clinician to the draw the anchor segments 26 together against the central segment 29 so that the segments 26 assume the second rigid state as illustrated in FIG. 3. To maintain the anchor segments in the rigid state, the filament actuators 42, 44 may be tied, sutured, or otherwise fixed externally to the body so that tension is maintained on the anchor segments 26.

The anchor segments 26, such as the individual cylindrical segments 28, may have flat end faces 30, 32 that are brought into abutting axial alignment upon a sufficient tension force being applied to the filaments 42, 44. In an alternate embodiment illustrated, for example in FIG. 5, the end faces of the cylindrical segments 28 include interengaging alignment structure 34 that aids in aligning and maining the cylindrical segments 28 in the second rigid state. The alignment structure 34 may include any suitable male/female engagement structure, such as a recess 38 defined in the second end face 32 of one cylindrical segment 28 that is engaged by a protrusion 36 in the first end face 30 of the adjacent cylindrical segment 28. The distal end of the shaft 16 may include protrusions 25 that engage into a recess 38 of the cylindrical segment 28 that is pulled into abutting engagement with the shaft 16, as particularly illustrated in FIG. 5.

Figure 6A:
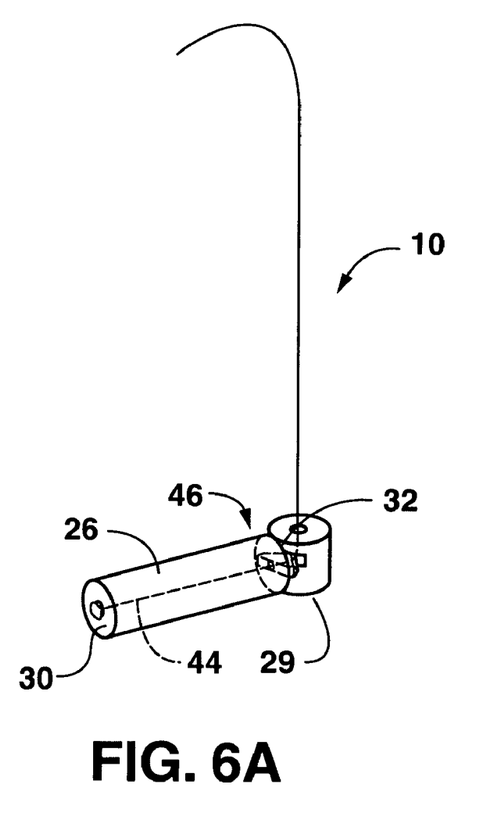
FIGS. 6A through 6C are various views of an alternative embodiment of an anchoring apparatus with anchor segments having alignment structure in the end faces thereof.
Figure 6B:
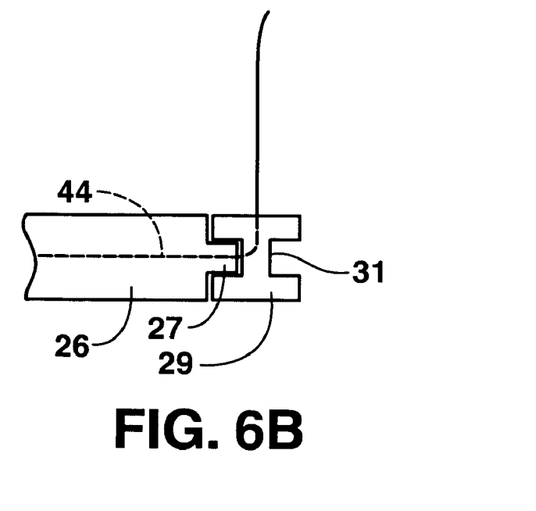
Figure 6C:
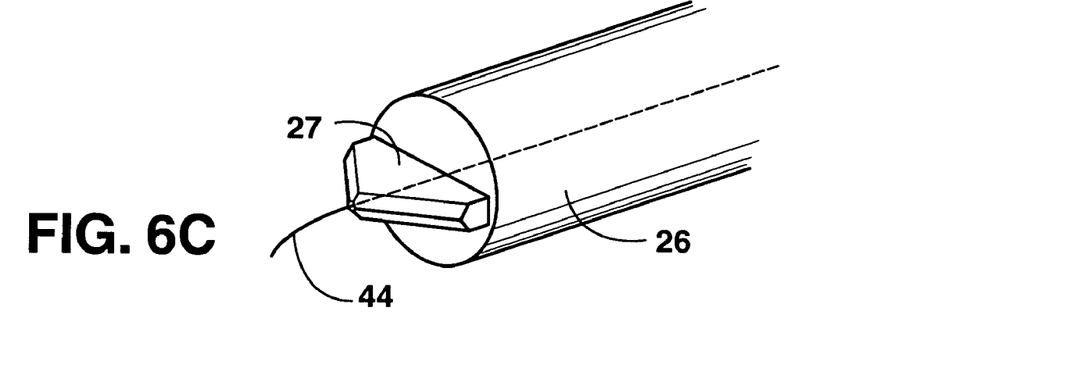

FIGS. 6A through 6C illustrate an alternative embodiment of interengaging structure between adjacent anchor segments 26. In this particular embodiment, the anchor segments 16 include a tapered protrusion 27 extending from the end face 32 thereof closest to the central segment 29. This protrusion 27 engages into a correspondingly shaped slot 31 formed in the central segment 29, as particularly illustrated in FIGS. 6A and 6B. Upon initial tensioning of the actuator filament 44, the end face 32 of the anchor segment 26 is drawn against the central segment 29 such that the protrusion 27 engages and slides into the recess 31. It should be appreciated that this configuration may be provided between adjacent faces of multiple anchor segments 26 within any branch of the segments. This type of protrusion/recess engagement may be desired in that it requires less tension on the actuator filaments 42, 44 to maintain the segments in the second rigid configuration.

The central segment 29 in the embodiment of FIGS. 6A through 6C is a cylindrical segment oriented vertically. It should be appreciated that this segment may be oriented horizontally as well.

The anchor segments 26 may be maintained in their second rigid state by a constant external tensioning force applied to the actuator filaments 42, 44, as with the embodiments of FIGS. 3 through 6. Upon release of the tensioning force, for example by cutting or releasing of the filaments 42, 44, the anchor segments 26 are free to assume their first relaxed state.

Figures 7A, 7B:
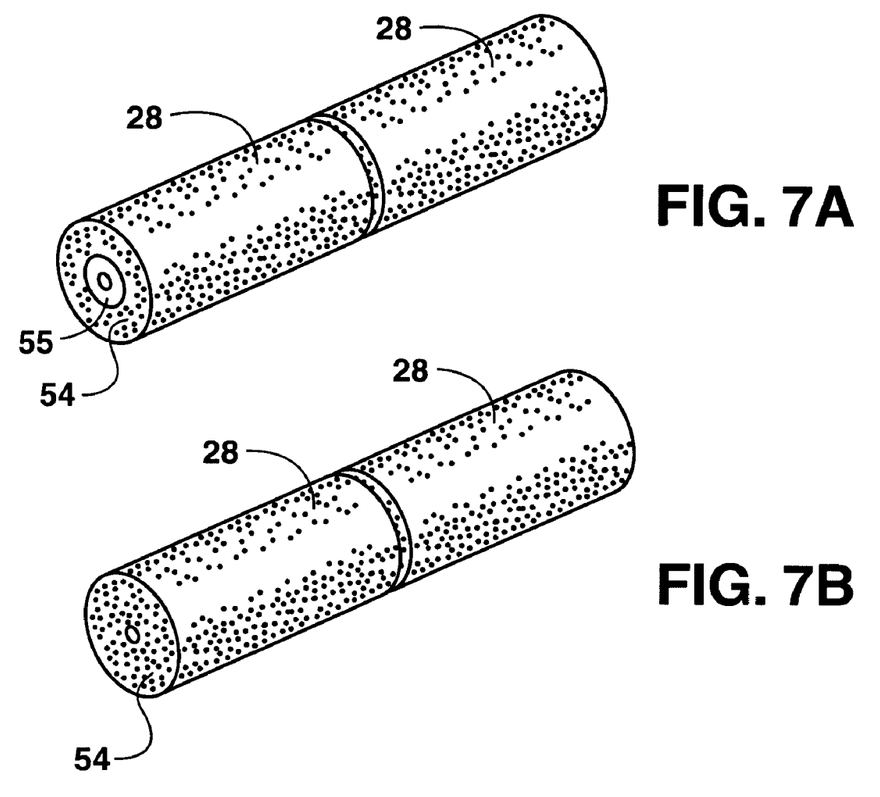
FIGS. 7A and 7B are perspective views of embodiments of anchor segments that incorporate a resorbable material in accordance with aspects of the invention.

FIG. 7A illustrates an embodiment of cylindrical segments 28 that may be used as anchor segments 26 wherein an outer circumferential portion of resorbable material 54 is formed around a polymeric core member 55 having the bore defined therethrough. Thus, after the resorbable material 54 breaks down, the central core portion 55 remains, but is relatively small and easily passed by the patient. In the embodiment of FIG. 7B, the entire cylindrical segments 28 are formed from the resorbable material 54. As discussed, the resorbable materials aid in collapsing and passing the apparatus components through the patient's digestive tract after the stoma has been formed in the tissue layers and the apparatus 10 is no longer needed. The resorbable components break down into small pieces that are easily passed through the patient's digestive tract with less chance of becoming lodged.

Figure 8:
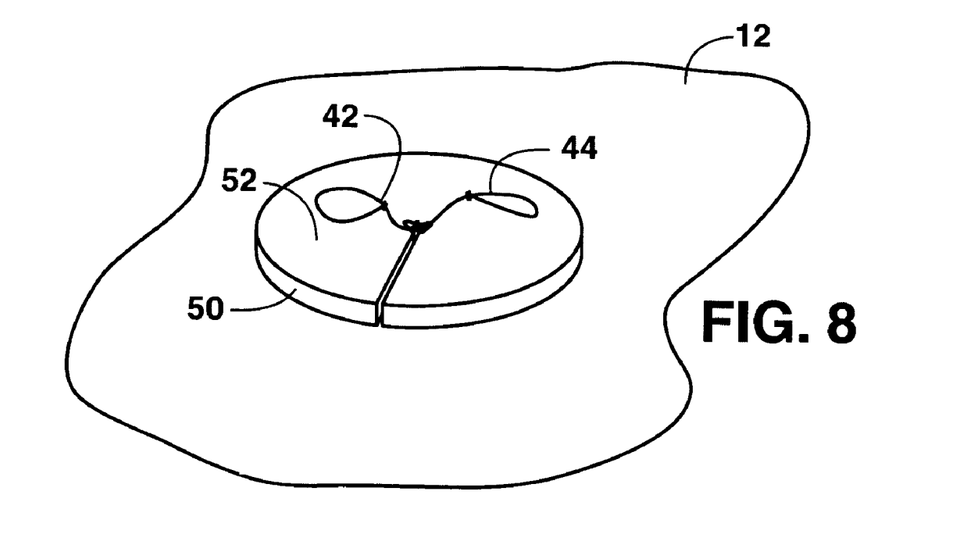
FIG. 8 is a perspective view of an embodiment of a fixing device that may be used to secure actuator filaments external to the patient.

Any manner of low profile external fixing member 48 (FIG. 8) may be used to receive the proximal end of the actuator filaments 42, 44 relative to the patient. In the embodiment of FIGS. 1 and 8, the external fixing member 48 is a relatively flat disc shaped member 50 having a slot or hole 52 formed therein through which the filaments 42, 44 are received. The actuator filaments 42, 44 may be tied off in a manner such that they are prevented from being pulled back through the body tissue layers. For example, the filaments 42, 44 may be tied or otherwise attached to the fixing member 48. An advantage of such a device is that the disc 50 can be made as thin as possible, for example on the order of 1 to 2 mm dependent upon the material from which the disc is manufactured. A fixing member 48 of this construction has a very low profile and is thus easily concealed by the application of a bandage over the patient's skin. This enables the apparatus 10 to be in place and performing its function without being noticeable to the public. Also, such a configuration assists in maintaining sterility of the site and minimizes the potential for inadvertent injury to the area.

In an alternative embodiment of a fixing member 48 not illustrated in the figures, a multicomponent design may be used wherein a base plate seats against the patient's body and receives the actuator filaments 42, 44 similar to the embodiment illustrated in FIG. 8. A lid or cap may be provided that secures over the base plate, as well as any portion of the shaft 16 protruding from the body.

Due to the collapsible nature of the apparatus 10, the removal process of the apparatus is far less traumatic as compared to prior art devices. In a first removal process, the actuator 40 is "released" (i.e. cut or untied from the external fixing member 48) such that the anchor segments 26 are no longer positively held in the second rigid state. The anchor segments 26 are free to separate and collapse into their first relaxed state wherein they are allowed to remain in the patient and are eventually passed by the patient, particularly in the embodiment wherein the anchor segments 26 are formed by even smaller individual cylindrical segments 28.

In still an alternate removal process, the actuator filaments 42, 44 are formed of a resorbable material that essentially disintegrates over time such that the anchor segments 26 are released from their rigid state and are passed by the patient. As mentioned, the segments 26 may also be formed of a resorbable material and allowed to essentially degrade and break into smaller pieces that are passed by the patient.

While the invention has been described in detail with respect to specific embodiments thereof, it should be appreciated by those skilled in the art that various alterations, modifications, and other changes may be made to the invention without departing from the scope and spirit of the invention. It is intended that the invention include all such modifications and alterations as encompassed by the appended claims.

What is claimed is:

1. An apparatus for insertion into a body orifice for anchoring a first body tissue layer to a second body tissue layer comprising:

a plurality of individual substantially rigid anchor segments for placement in a body cavity, said anchor segments having a first relaxed state wherein said segments are movable relative to each other and alignable along a common initial longitudinal axis for initial placement of said apparatus through the body tissue layers, said anchor segments having a second rigid state wherein said segments assume a rigid end-to-end abutting configuration relative to each other along a final common longitudinal axis and at a transverse angle relative to said initial longitudinal axis; and an actuator connected to said anchor segments and configured to extend through the tissue layers to an external location, said actuator externally manipulated to configure said anchor segments between said first relaxed state and said second rigid state wherein said anchor segments are drawn together in said abutting relationship along said final common longitudinal axis; wherein said plurality of individual substantially rigid anchor segments comprises at least two anchor segments and a center anchor segment, one of said at least two anchor segments extending in a first transverse direction from said center anchor segment, and the other of said at least two anchor segments extending in a second opposite transverse direction from said center anchor segment; and wherein the actuator comprises a filament associated with each said anchor segment extending in each transverse direction and terminating at the distal end of each anchor segment.

2. The apparatus of claim 1, wherein said filaments pass through said center anchor segment.

3. The apparatus of claim 2, comprising a plurality of said anchor segments extending in each transverse direction, said anchor segments disconnected and movable relative to each other in said first relaxed state.

4. The apparatus of claim 3, wherein said anchor segments comprise engaging alignment structure at end faces thereof.

5. The apparatus of claim 1, wherein said anchor segments comprise substantially cylindrical segments with said actuator passing therethrough and anchored to a last one of said anchor segments extending in opposite transverse directions from said initial longitudinal axis.

6. The apparatus of claim 1, wherein said anchor segments are maintained in said second rigid state by an external tensioning force applied to said actuator, and whereupon said anchor segments assume said first relaxed state upon release of said tensioning force.

7. The apparatus of claim 1, further comprising an external fixing member configured to secure said actuator in position relative to the patient.

8. The apparatus of claim 1, wherein at least a portion of said anchoring segments are made from a resorbable material such that over time said anchoring segments decrease in size within a patient.

9. The apparatus of claim 8, wherein said anchoring segments are formed substantially entirely from said resorbable material.

10. The apparatus of claim 1, wherein said actuator is formed from a resorbable material that breaks down over time in a patient, whereupon said anchor segments become disconnected from said actuator.

11. The apparatus of claim 1, wherein any combination of said actuator and said anchor segments are made from a resorbable material that breaks down over time in a patient.

12. An apparatus for insertion into a body orifice for anchoring a first body tissue layer to a second body tissue layer comprising:

a plurality of individual anchor segments having individual passages therethrough, said anchor segments having a first relaxed state wherein said segments are movable relative to each other and alignable along an initial common longitudinal axis for initial placement of said apparatus through the body tissue layers, said anchor segments having a second rigid state wherein said segments assume a rigid end-to-end abutting configuration relative to each other along a final common longitudinal axis at a transverse angle relative to said initial longitudinal axis such that a set of at least two of said anchor segments extend in generally opposite transverse directions from a central anchor segment, said anchor segments disconnected and movable relative to each other in said first relaxed state; and a filament actuator connected to each set of said transversely extending anchor segments, said filament actuators extending through said central anchor segment and through said passages in said anchor segments and terminating at a last one of said anchor segments in each transverse direction, said actuator filaments being externally manipulated to configure said anchor segments between said first relaxed state and said second rigid state wherein said sets of anchor segments are drawn together in said abutting relationship along said final common longitudinal axis at opposite transverse sides of said center anchor segment.

13. The apparatus of claim 12, wherein said anchor segments comprise engaging alignment structure at end faces thereof.

14. The apparatus of claim 12, wherein said anchor segments are maintained in said second rigid state by an external tensioning force applied to said actuator, and whereupon said anchor segments assume said first relaxed state upon release of said tensioning force.

15. The apparatus of claim 12, wherein at least a portion of said anchoring segments are made from a resorbable material that breaks down over time in a patient such that said anchoring segments decrease in size within the patient.

16. The apparatus of claim 12, wherein said actuator filaments are formed from a resorbable material that breaks down over time in a patient, whereupon said anchor segments become disconnected from said shaft.

17. The apparatus of claim 12, wherein any combination of said actuator and said anchor segments are made from a resorbable material that breaks down over time in a patient.

* * * * *